United States Patent
Alaluf et al.

(10) Patent No.: US 6,403,064 B1
(45) Date of Patent: *Jun. 11, 2002

(54) SKIN LIGHTENING COMPOSITION

(75) Inventors: Simon Alaluf; Martin Richard Green, both of Bedford (GB); Koichi Iwata, Edgewater, NJ (US); Gerald Patrick McNeill, Channahon, IL (US); Jonathan Richard Powell, Bedford; Anthony Vincent Rawlings, Bebington, both of (GB)

(73) Assignee: Unilever Home & Personal Care USA Division of Conopco, Inc., Greenwich, CT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/467,426

(22) Filed: Dec. 20, 1999

(30) Foreign Application Priority Data

Dec. 22, 1998 (GB) ................................. 9828380

(51) Int. Cl.$^7$ .......................... A61K 7/42; A61K 7/135; A61K 7/00
(52) U.S. Cl. ............................. 424/62; 424/401; 424/59
(58) Field of Search .............................. 424/59, 402, 62

(56) References Cited

U.S. PATENT DOCUMENTS

| | | | |
|---|---|---|---|
| 4,990,330 A | 2/1991 | Oyama | 424/59 |
| 5,208,356 A | 5/1993 | Pariza et al. | 554/79 |
| 5,585,400 A | 12/1996 | Cook et al. | 514/560 |
| 6,019,990 A | 2/2000 | Remmereit | 424/401 |

FOREIGN PATENT DOCUMENTS

| | | |
|---|---|---|
| GB | 2 126 892 A | 4/1984 |
| GB | 2 287 405 | 9/1995 |
| JP | 63284119 | 5/1987 |
| JP | 6199646 | 12/1992 |
| WO | 94/07462 | 4/1994 |
| WO | 94/09756 | 5/1994 |
| WO | 97/18320 | 5/1997 |
| WO | 98/17269 | 4/1998 |

OTHER PUBLICATIONS

PCT Search Report # GB 9828380.7.
Chemical Abstract 111–160007.

*Primary Examiner*—Thurman K. Page
*Assistant Examiner*—Brian K. Seidleck
(74) *Attorney, Agent, or Firm*—Ellen Plotkin

(57) ABSTRACT

A topical composition comprising:
(a) conjugated linoleic acid, and/or derivatives thereof comprising conjugated linoleic acid moieties, in which at least 1% by weight of the conjugated linoleic acid and/or moieties is present as the trans 10, cis 12 isomer, and
(b) a dermatologically acceptable carrier. The product is particularly suitable for lightening human skin.

4 Claims, No Drawings

SKIN LIGHTENING COMPOSITION

The invention relates to topical compositions for application to human skin and to their use in lightening human skin.

BACKGROUND AND PRIOR ART

Many people are concerned with the degree of pigmentation of their skin. For example, people with age spots or freckles may wish such pigmented spots to be less pronounced. Others may wish to reduce the skin darkening caused by exposure to sunlight or to lighten their natural skin colour. To meet this need many attempts have been made to develop products that reduce the pigment production in the melanocytes. However, the substances thusfar identified tend to have undesirable side effects, e.g. skin irritation. Consequently such substances are not suitable for cosmetic use or they can only be applied at a concentration at which their skin lightening effect is less than desired. Using a combination of different skin lightening substances may be considered to reduce adverse side effects but there is a substantial risk that by using such a combination the skin lightening is reduced as well due to competition effects. Therefore there is a need for improvement in the effectiveness of cosmetic skin lightening products.

GB 2 287 405 discloses a skin-whitening cosmetic preparation that comprises in combination an extract of Glycyrrhyza glabra or a related plant species and an α-hydroxy-, β-hydroxy- or keto-acid or an amide, salt or ester thereof. The combination is said to act synergistically to inhibit tyrosinase thus inhibiting melanin formation.

WO 94/07462 discloses compositions inter alia to lighten the skin that comprise retinol or a derivative thereof and a dioic acid.

WO 94/09756 proposes the use of retinol or a derivative thereof together with a selected skin lightening agent for several purposes including lightening skin colour. The preferred skin lightening agent is hydroquinone but several others are mentioned as well, including liquorice extract.

U.S. Pat. No. 4,990,330 describes skin-whitening products that contain kojic acid in combination with another substance to be chosen from a range of materials including azelaic acid. The combination is reported to synergistically inhibit melanin synthesis.

JP 63284119 according to the Derwent abstract proposes a skin external agent with UV-preventing and whitening effects that contains isoferulic acid or a salt thereof and an organic acid or a salt thereof.

J06199646 according to the Derwent abstract describes a cosmetic to whiten skin that contains a plant extract, urea and a urea stabiliser. The extract can be chosen from a wide range of plants including glycyrrhizae radix (licorice root). The urea stabiliser can likewise be chosen from a broad group which group includes aliphatic dicarboxylic acids.

The above described products have thusfar not found wide acceptance and there continues to be a need for improvement in the area.

We have now found that enhanced reduction of melanin production can be obtained through the application of cosmetic compositions to the skin which comprise a specific isomer of conjugated linoleic acid or derivatives thereof.

SUMMARY OF THE INVENTION

According to a first aspect of the present invention there is provided a topical composition comprising:
  (a) conjugated linoleic acid, and/or derivatives thereof comprising conjugated linoleic acid moieties, in which at least 1% by weight of the conjugated linoleic acid and/or moieties is present as the trans 10 cis 12 isomer; and
  (b) a dermatologically acceptable vehicle.

Such compositions are particularly useful for topical application to human skin for enhancing the reduction of melanin production and thus lightening the skin on which it has been applied.

According to a second aspect, the present invention provides a cosmetic method for lightening human skin, the method comprising application to the skin of a topical composition as described above.

In a further aspect, the invention also provides the use of conjugated linoleic acid, and/or derivatives thereof comprising conjugated linoleic acid moieties, in a topical composition for lightening human skin, wherein at least 1% by weight of the conjugated linoleic acid and/or moieties is present as the trans 10 cis 12 isomer.

In a still further aspect of the invention, the reversal of the skin lightening action of the above described conjugated linoleic acid and/or derivatives is avoided through inclusion of an ultraviolet absorbing sunscreen in the compositions according to the first aspect of the present invention. By the term "sunscreen" is meant any material whether organic or inorganic which can shield the skin from ultraviolet radiation within the range of 290 to 400 nm.

DETAILED DESCRIPTION OF THE INVENTION

Trans 10, Cis 12 Isomer Containing Conjugated Linoleic Acid

Conjugated linoleic acid(hereinafter described as CLA) comprises a group of positional and geometric isomers of linoleic acid in which various configurations of cis and trans double bonds at positions (6, 8), (7, 9), (8, 10), (9, 11), (10, 12) or (11, 13) are possible. Thus twenty-four different isomers of the CLA exist.

The essential active of the compositions in accordance with the present invention is the trans 10 cis12 (hereinafter referred to as t10 c12) isomer. This particular isomer of the free acid has the structure (I) shown below:

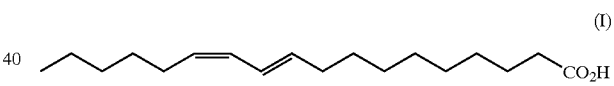

(I)

The invention also includes derivatives of the free acid which thus comprise conjugated linoleic acid moieties. Preferable derivatives include those derived from substitution of the carboxyl group of the acid, such as esters (eg retinyl esters, triglyceride esters, monoglyceride esters, diglyceride esters, phosphoesters), amides (eg ceramide derivatives), salts (eg alkali metal and alkali earth metal salts, ammonium salts); and/or those derived from substitution of the C18 carbon chain, such as alpha hydroxy and/or beta hydroxy derivatives.

In the case of triglyceride ester derivatives, all positional isomers of CLA substituents on the glycerol backbone are included. The triglycerides must contain at least one CLA moiety. For example, of the three esterifiable positions on the glycerol backbone, the 1 and 2 positions may be esterified with CLA and by another lipid at position 3 or as an alternative, the glycerol backbone could be esterified by CLA at the 1 and 3 positions with another lipid at position 2.

Wherever the term "conjugated linoleic acid" or "CLA" is used in this specification it is to be understood that the derivatives thereof comprising CLA moieties are also included.

"CLA moieties" refers to the CLA fatty acyl portion(s) of a CLA derivative.

By "t10 c12 isomer containing CLA" is meant that at least 1% by weight of the total CLA and/or CLA moieties present in the composition is in the form of the trans 10, cis 12 isomer. Preferably, at least 20%, most preferably at least 50%, by weight of the total CLA and/or moieties present in the composition, is in the form of the t10 c12 isomer. In a particularly preferred embodiment at least 70% by weight of the total CLA and/or moieties is in the form of the t10 c12 isomer.

The CLA and/or derivatives thereof comprising CLA moieties according to the present invention may be prepared according to the method disclosed in WO 97/18320. A preferred method of preparation is disclosed in Example 1 below.

The active, t10 c12 isomer containing CLA, to be employed in accordance with the present invention is present in the topical composition in an effective amount. Normally the total amount of the active is present in an amount between 0.00001% and 50% by weight of the composition. More preferably the amount is from 0.01% to 10% and most preferably from 0.1% to 5% in order to maximise benefits at a minimum cost.

Dermatologically Acceptable Vehicle

The composition according to the invention also comprises a dermatologically/cosmetically acceptable vehicle to act as a dilutant, dispersant or carrier for the active, t10, c12 isomer enriched CLA. The vehicle may comprise materials commonly employed in skin care products such as water, liquid or solid emollients, silicone oils, emulsifiers, solvents, humectants, thickeners, powders, propellants and the like.

The vehicle will usually form from 5% to 99.9%, preferably from 25% to 80% by weight of the composition, and can, in the absence of other cosmetic adjuncts, form the balance of the composition.

Optional Skin Benefit Materials and Cosmetic Adjuncts

Besides the active, t10, c12 isomer containing CLA, other specific skin-benefit actives such as sunscreens, and/or other skin lightening agents, may also be included. When the sunscreen is an organic material, it will usually contain at least one chromophoric agent absorbing within the ultraviolet range somewhere from 290 to 400 nm. Chromophoric organic sunscreen agents may be divided into the following categories (with specific examples) including: p-Aminobenzoic acid, its salts and its derivatives (ethyl, isobutyl, glyceryl esters; p-dimethylaminobenzoic acid); Anthranilates (o-aminobenzoates; methyl, methyl, phenyl, benzyl, phenylethyl, linalyl, terpinyl, and cyclohexenyl esters); Salicylates (octyl, amyl, phenyl, benzyl, menthyl, glyceryl, and dipropyleneglycol esters); Cinnamic acid derivatives (menthyl and benzyl esters, a-phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naptholsulfonates (sodium salts of 2-naphthol-3,6-disulfonic and of 2-naphthol-6,8-disulfonic acids); Dihydroxy-napthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride oleate and tannate); Quinoline derivatives (8-hydroxyquinoline salts, 2-phenylquinoline); Hydroxy- or methoxy-substituted benzophenones; Uric and vilouric acids; Tannic acid and its derivatives (e.g. hexaethylether); (Butyl carbityl) (6-propyl piperonyl) ether; Hydroquinone; Benzophenones (Oxybenzone, Sulisobenzone, Dioxybenzone, Benzoresorcinol, 2,2', 4,4'-Tetrahydroxybenzophenone, 2,2'-Dihydroxy-4,4'-dimethoxybenzophenone, Octabenzone; 4-isopropyldibenzoylmethane, Butylmethoxydibenzoylmethane; Etocrylene; and 4-isopropyl-dibenzoylmethane).

Particularly useful are: 2-ethylhexyl p-methoxycinnamate,4,4'-t-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone, ethyl-4-[bis(hydroxypropyl)] aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl)-5-sulfoniobenzoxazoic acid and mixtures thereof.

Suitable commercially available organic sunscreen agents are those identified under the following table.

TABLE I

| CTFA NAME | TRADE NAME | SUPPLIER |
|---|---|---|
| Benzophenone-3 | UVINUL M-40 | BASF Chemical Co. |
| Benzophenone-4 | UVINUL MS-40 | BASF Chemical Co. |
| Benzophenone-8 | SPECTRA-SORB UV-24 | American Cyanamid |
| DEA-Methoxycinnamate | BERNEL HYDRO | Bernel Chemical |
| Ethyl dihydroxypropyl-PABA | AMERSCREEN P | Amerchol Corp. |
| Glyceryl PABA | NIPA G.M.P.A. | Nipa Labs. |
| Homosalate | KENESTER HMS | Humko Chemical |
| Menthyl anthranilate | SUNAROME UVA | Felton Worldwide |
| Octocrylene | UVINUL N-539 | BASF Chemical Co. |
| Octyl dimethyl PABA | AMERSCOL | Amerchol Corp. |
| Octyl methoxycinnamate | PARSOL MCX | Bernel Chemical |
| Octyl salicylate | SUNAROME WMO | Felton Worldwide |
| PABA | PABA | National Starch |
| 2-Phenylbenzimidazole-5-sulphonic acid | EUSOLEX 6300 | EM Industries |
| TEA salicylate | SYBARINE W | Felton Worldwide |
| 2-(4-Methyl-benzlidene)-camphor | EUSOLEX 6300 | EM Industries |
| Benzophenone-1 | UVINUL 400 | BASF Chemical Co. |
| Benzophenone-2 | UVINUL D-50 | BASF Chemical Co. |
| Benzophenone-6 | UVINUL D-49 | BASF Chemical Co. |
| Benzophenone-12 | UVINUL 408 | BASF Chemical Co. |
| 4-Isopropyl dibenzoyl methane | EUSOLEX 8020 | EM Industries |
| Butyl Methoxy dibenzoyl methane | PARSOL 1789 | Givaudan Corp. |
| Etocrylene | UVINUL N-35 | BASF Chemical Co. |

Inorganic sunscreen actives may also be employed such as microfine titanium dioxide, zinc oxide, polyethylene, polyamides (e.g. nylon) and various other polymers. Amounts of the sunscreen agents (whether organic or inorganic) will generally range from 0.1 to 30%, preferably from 2 to 20%, optimally from 4 to 10% by weight.

The vehicle may also further include adjuncts such as perfumes, anti-oxidants, opacifiers, preservatives, colourants and buffers.

Product Preparation, Form, Use and Packaging

To prepare the topical composition according to the present invention the usual manner for preparing skin care products may be employed. The active components are generally incorporated in a dermatologically acceptable carrier in conventional manner. The active components can suitably first be dissolved or dispersed in a portion of the water or another solvent or liquid to be incorporated in the composition. The preferred compositions are oil-in-water or water-in-oil emulsions.

The composition may be in the form of conventional skin-care products such as a cream, gel or lotion or the like. The composition can also be in the form of a so-called "wash-off" product e.g. a bath or shower gel, possibly containing a delivery system for the actives to promote adherence to the skin during rinsing. Most preferably the product is a "leave-on" product; a product to be applied to the skin without a deliberate rinsing step soon after its application to the skin.

The composition may packaged in any suitable manner such as in a jar, a bottle, tube, roll-ball, or the like, in the conventional manner.

The product can be applied to the skin in the same way as conventional skin care products. e.g. it can be applied 1–3 times daily to the skin of e.g. the face and/or the hands and arms. In case of pigmented spots, the user may for example choose to apply the product only to the affected areas. The skin lightening will usually become visible after 2–3 months depending on the skin condition, the concentration of active components in the product and the amount of product and the frequency with which it is applied. The present product is particularly suitable for general skin lightening, especially if it also includes sunscreen agent in case the product is intended for daytime use.

In order that the present invention may be more readily understood, the following examples are given, by way of illustration only.

EXAMPLES

Example 1

This example illustrates synthesis of CLA comprising 80.5% t10 c12 isomer by weight of total CLA moieties, a compound included in the scope of the present invention Mixed isomers of CLA are prepared by high temperature alkali treatment of Safflower oil, generating CLA with equal amounts of the c9,t11 and t10,c12 CLA isomers. CLA enriched in the c9,t11 CLA is separated from the mix by selective esterificaton with lauryl alcohol using Geotrichum Candidum as a catalyst. After the esterification step and separation the remaining CLA free acids are enriched in t10,c12 CLA and isolated.

Production of Mixed Isomers of CLA

'Analar Reagent' (AR) sodium hydroxide (0.6 kg) was dissolved in 6 kg of pharmaceutical grade propylene glycol by mixing and heating to 80–85° C. The sample was cooled and 2 kg of safflower oil was added. Using standard pilot scale equipment the mixture was refluxed for 3 hours with fast stirring at 170° C. The reaction mix was cooled to about 95° C., the stirrer reduced to an intermediate speed, and the mix neutralised using 1.280 liter of 35.5% hydrochloric acid dissolved in demineralised water (8 liters), keeping the temperature at about 90° C. The reaction mix was allowed to settle and the aqueous phase was run off. The oil phase was washed with 2×1 liter of 5% AR salt solution and by 2×1 liter of demineralised water at 90° C., discarding any soapy material. The CLA enriched oil was dried at 1000° C. under vacuum before draining at about 50° C. and filtered through a buchner system containing a Whatman filter and a thin layer of celite-hyflo-filter aid. The mixed isomer CLA oil was stored under nitrogen at −25° C. until required.

Production of Enriched CLA c9 t11

(I) Preparation of Lauryl Esters

CLA prepared from Safflower (2.0 kg) was added to 2×molar equivalents of lauryl alcohol (1-dodecanol; 98% ex Aldrich chemicals) along with 5.96 kg of demineralised water. The temperature was adjusted to 25° C. and 1% (w/w) of Geotrichum Candidum (ex Amano Pharmaceuticals, Japan) was added premixed with a little water, and mixed vigorously. The reaction was stopped at 44 hours. The vessel was heated to 80–90° C., the aqueous layer drained and the oil was washed with demineralised water and dried at 100° C. under vacuum for 30 minutes. The oil was cooled to 50° C. and filtered through a buchner system containing a Whatman filter and a thin layer of celite-hyflo-filter aid.

(II) Separation of the Enriched t10, c12 CLA:

Residual lauryl alcohol was removed at 130° C. at 25–35 ml per minute by molecular distillation. The residue was coarsely separated into the lauryl esters (enriched in c9,t11 CLA) and free acids (enriched in t10,c12 CLA) by evaporation at 158° C. at a flow rate of 25–35 ml per minute.

Isolation of the Enriched t10,c12 CLA

The CLA free acids from step (II) above were distilled again at 160–165° C. and 20–30 ml/min to reduce the ester content. Residual lauryl alcohol was reduced further by a distillation at 131° C. and 25–30 ml/min flow rate. In order to remove any residual lauryl alcohol, free alcohols were esterified to the fatty acids present in the reaction mix, using SP392 *Mucor miehei* lipase (5%, batch lux 0110 ex Novo Nordisk). The enriched t10,c12 CLA containing fatty acids were separated from the lauryl esters using molecular distillation under vacuum at 155° C. at 15–20 ml per minute. The composition of the enriched t10,c12 CLA generated by this method is set out in table 1 below:

TABLE 1

| Composition of typical preparation of enriched t10.c12 CLA fatty acids (wt %): | B |
|---|---|
| c9,t11 | 8.3 |
| t10,c12 | 53.9 (80.5% of total CLA) |
| c9,c11 & c10,c12 | 2.9 |
| t9,t11t & t10,12t | 1.1 |
| Other CLA | 0.7 |
| Total CLA | 66.9 |
| 16:0 | 13.6 |
| 16:1 | — |
| 18:0 | 4.6 |
| 18:1 | 10.3 |
| 18:2 (non-CLA) | 3.1 |
| Other fatty acid | 1.5 |

Example 2

Preparation of t10, c12 CLA Triglycerides

Enriched t10, c12 CLA (10 g) prepared according to example 1 was mixed with 1.01 g (10.1%) of glycerol (Pricerine 9083 glycerine CP from Ellis and Everards) and 0.5 g (approximately 5%) of SP392 *Mucor Meihie* non-specific lipase (Mucor Meihie Ex Novo Nordisk Batch Lux 0110) was added. The mixed materials were stirred under vacuum in a rotary-evaporator at 60° C. with a slight nitrogen bleed.

After 96 hours the reaction was stopped by filtering the mixture through a thin layer of celite super-cel filter aid on a buchner filter collecting the CLA triglyceride oil phase, the composition of which is set out in table 2 below:

TABLE 2

| Fatty Acid composition of the triglycerides | Relative Percentage of Total fatty acid Lipid |
|---|---|
| c9,t11 | 8.3 |
| t10,c12 | 54.8 (81.7% of total CLA) |
| c9,c11 & c10,c12 | 2.7 |
| t9,t11t & t10,12t | 1.3 |
| Other CLA | 0 |
| Total CLA | 67.1 |
| 16:0 | 13.5 |
| 16:1 | 0.1 |
| 18:0 | 4.9 |
| 18:1 | 10.3 |
| 18:2 (non-CLA) | 3.4 |
| Other fatty acid | 0.7 |

Example 3

Assay Methodology

Cell Maintenance

B16-F1 mouse melanoma cells (American Type Culture Collection, Maryland, USA) were maintained in 75 cm² culture flasks in RPMI 1640 medium (ICN-Flow, cat. no. 12-60-54) supplemented with L-glutamine (4 mM) and 10% foetal bovine serum (FBS) at 37 LC in a water saturated, 5% $CO_2$ in air atmosphere. Cells were passaged twice weekly.

Pigmentation Assay

Subconfluent B16 cells were seeded in 96 well microtiter plates at a density of 5000 cells/well and cultured overnight in DMEM (Life Technologies, NY) containing 10% foetal bovine serum and 1% penicillin/streptomycin without phenol red at 37° C. under 5% CO2. After 24 hours, the media was replaced with fresh media containing the test materials or vehicle controls. Cells were incubated for 72 hours at which time melanin was visible in the control wells. Next, the melanin containing media from each well was transferred to a clean 96 well plate and quantified by reading the absorbance at 530 nm using a microplate spectrophotometer (Dynatech MR5000) and correcting for the baseline absorption of fresh medium. As the corrected absorption is proportional to the melanin concentration the percentage pigmentation for a skin lightening test substance can be calculated as:

% pigmentation=($OD_{530}$ test/$OD_{530}$ ref)×100% where $OD_{530}$ test and $OD_{530}$ ref indicate the average corrected absorption of the medium from the wells with the test substance and that of the medium from the wells without the test substance. The percentage inhibition caused by the test substance is then 100—% pigmentation.

Cell viability assay

Melanin production may be reduced by inhibition of melanogenesis but it may also be affected by cytotoxicity or cell proliferation. To test whether this occurred cell viability was tested by neutral red dye absorption. Neutral red is a water soluble dye that passes through the intact plasma membrane and becomes concentrated in the lysosomes in intact cells. Total neutral red dye uptake is proportional to the number of viable cells in culture.

Immediately following the removal of medium for melanin analysis from the microtitre wells, 200 µl fresh pre-warmed neutral red dye (ex. Sigma, UK, Cat. Nr 2889) at 25 µg/ml medium was applied to the cells and incubated for 3 hours as for cell maintenance. Dye which had not been taken up by the cells was removed by inversion of the plate and tapping on absorbent paper. The cells were washed with 200 µl PBS, which was then removed again. 100 µl solvent (50% $H_2O$, 49% ethanol, 1% acetic acid) was added. After 20 minutes at ambient temperature each plate was shaken for 5 seconds on a microtitre plate shaker. The absorption was measured as described above.

Tests

Table 3 below indicates the skin lightening test substances evaluated and the amount in which they were applied. The percentage inhibition of melanin production caused by the test substances as described above is reflected in the table as well.

Values less than 100% melanin control indicate inhibition of melanogenesis. Thus the results in Table 3 show that CLA containing the t10 c12 isomer of CLA inhibits melanin production.

In the trials the test substance was diluted with DMEM in the amounts shown in table 3 below.

"CLA t10 c12" in the table refers to CLA in which 80.5% by weight of the total CLA is the t10 c12 isomer i.e. an active agent that is within the scope of the present invention. This was prepared as described in example 1 above.

TABLE 3

| | Melanin in Media | | | Neutral Red Cell Viability | | |
|---|---|---|---|---|---|---|
| Treatment | % Control | S.D. | t-Test vs Control | % Control | S.D. | t-Test vs Control |
| Control | 100 | 8.5 | | 100.0 | 4.6 | |
| 1:100 t10, c12 CLA | 4.0 | 0.9 | ** (0.000) | 1.2 | 0.6 | ** (0.000) |
| 1:250 t10, c12 CLA | 4.2 | 0.8 | ** (0.000) | 89.5 | 3.5 | ** (0.000) |
| 1:500 t10, c12 CLA | 4.0 | 0.5 | ** (0.000) | 90.4 | 3.3 | ** (0.000) |
| 1:750 t10, c12 CLA | 9.7 | 11.5 | ** (0.000) | 97.6 | 7.2 | (0.257) |
| 1:1000 t10, c12 CLA | 9.8 | 6.4 | ** (0.000) | 96.2 | 4.4 | * (0.042) |

Student's t-Test
** $p < 0.01$
* $p < 0.05$ (n = 4)

Example 4

The formulation below describes an emulsion cream according to the present invention.

| FULL CHEMICAL NAME OR CTFA NAME | TRADE NAME | WT. % |
|---|---|---|
| CLA triglyceride (80.5% t10 c12 isomer by weight of total CLA moieties made according to example 2 | | 2.0 |
| disodium EDTA | Sequesterene Na2 | 0.05 |
| magnesium aluminium silicate | Veegum Ultra | 0.6 |
| methyl paraben | Methyl Paraben | 0.15 |
| simethicone | DC Antifoam Emulsion | 0.01 |
| butylene glycol 1,3 | Butylene Glycol 1,3 | 3.0 |
| hydroxyethylcellulose | Natrosol 250 HHR | 0.5 |

-continued

| FULL CHEMICAL NAME OR CTFA NAME | TRADE NAME | WT. % |
|---|---|---|
| glycerine, USP | Glycerine USP | 2.0 |
| xanthan gum | Keltrol 1000 | 0.2 |
| triethanolamine | Triethanolamine (99%) | 1.2 |
| stearic acid | Pristerene 4911 | 3.0 |
| propyl paraben NF | Propylparaben NF | 0.1 |
| glyceryl hydrostearate | Naturechem GMHS | 1.5 |
| stearyl alcohol | Lanette 18 DEO | 1.5 |
| isostearyl palmitate | Protachem ISP | 6.0 |
| C12–15 alcohols octanoate | Hetester FAO | 3.0 |
| dimethicone | Silicone Fluid 200 (50 cts) | 1.0 |
| cholesterol NF | Cholesterol NF | 0.5 |
| sorbitan stearate | Sorbitan Stearate | 1.0 |
| butylated hydroxytoluene | Embanox BHT | 0.05 |
| tocopheryl acetate | Vitamin E Acetate | 0.1 |
| PEG-100 stearate | Myrj 59 | 2.0 |
| sodium stearoyl lactylate | Pationic SSL | 0.5 |
| hydroxycaprylic acid | Hydroxycaprylic Acid | 0.1 |
| retinyl palmitate | Vitamin A Palmitate | 0.06 |
| alpha-bisabolol | Alpha-bisabolol | 0.2 |
| water, DI | | q.s. to 100 |

Example 5

A skin cream (oil in water type) with sunscreen formulation according to the present invention is outlined below:

| INGREDIENT | WEIGHT (%) |
|---|---|
| Hydroxyethylcellulose | 0.50 |
| Magnesium Aluminum Silicate | 0.75 |
| Cocoa Butter | 1.25 |
| Squalene | 1.05 |
| Isostearyl Isononanoate | 2.25 |
| DC Silicone Fluid 200 ® (50 CST) | 1.25 |
| DC Silicone Fluid 200 ® (100 CST) | 0.50 |

-continued

| INGREDIENT | WEIGHT (%) |
|---|---|
| Butylene Glycol | 3.00 |
| Parsol MCX ® | 3.00 |
| Parsol 1789 ® | 3.00 |
| Glycerin | 2.50 |
| Sodium Hyaluronate | 0.50 |
| CLA triglyceride t10c12 | 5.00 |
| Glycereth-7 Hydroxystearate | 1.50 |
| Stearic Acid | 3.50 |
| Cetyl/Stearyl Alcohol | 2.55 |
| Sodium PCA | 2.10 |
| Glyceryl Hydroxystearate | 1.25 |
| Tocopherol | 0.35 |
| Methylparaben | 0.20 |
| Propylparaben | 0.10 |
| Glydant ® | 0.30 |
| Steareth-20 | 1.20 |
| Disodium EDTA | 0.05 |
| Triethanolamine | 1.50 |
| Deionized Water | Q.S |

What is claimed is:

1. A topical skin lightening composition comprising:

(a) about 0.1 to about 5% by weight conjugated linoleic acid and/or derivatives thereof consisting of conjugated linoleic acid moieties, in which at least 70% by weight of the conjugated linoleic acid and/or moieties is present as the trans 10, cis 12 isomer, and (b) a dermatologically acceptable carrier.

2. A composition according to claim 1 comprising 0.00001% to 50%, preferably 0.01% to 10% by weight of the composition of said conjugated linoleic acid and/or derivatives.

3. A composition according to claim 1 that also comprises a sunscreen.

4. A cosmetic method for lightening human skin, the method comprising applying to the skin a topical composition according to claim 1.

* * * * *